US010358405B2

(12) United States Patent
Dickey et al.

(10) Patent No.: US 10,358,405 B2
(45) Date of Patent: *Jul. 23, 2019

(54) MYRICANOL DERIVATIVES AND USES THEREOF FOR TREATMENT OF NEURODEGENERATIVE DISEASES

(71) Applicants: UNIVERSITY OF SOUTH FLORIDA, Tampa, FL (US); The United States of America as represented by the Department of Veterans Affairs, Washington, DC (US); Adria Dickey, Lutz, FL (US)

(72) Inventors: Chad Dickey, Lutz, FL (US); Umesh Jinwal, Tampa, FL (US); Laurent Calcul, Tampa, FL (US); Bill J. Baker, Tampa, FL (US); Matthew Lebar, Boston, MA (US)

(73) Assignees: UNIVERSITY OF SOUTH FLORIDA, Tampa, FL (US); THE UNITED STATES OF AMERICA AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/993,232

(22) Filed: May 30, 2018

(65) Prior Publication Data
US 2018/0265442 A1 Sep. 20, 2018

Related U.S. Application Data

(60) Division of application No. 15/414,242, filed on Jan. 24, 2017, which is a continuation of application No. 14/390,960, filed as application No. PCT/US2013/035628 on Apr. 8, 2013, now Pat. No. 9,598,338.

(60) Provisional application No. 61/678,409, filed on Aug. 1, 2012, provisional application No. 61/621,278, filed on Apr. 6, 2012.

(51) Int. Cl.
A61K 31/05 (2006.01)
A61K 31/11 (2006.01)
A61K 31/121 (2006.01)
C07C 43/21 (2006.01)
C07C 43/215 (2006.01)
C07C 43/23 (2006.01)
C07C 47/277 (2006.01)
C07C 69/28 (2006.01)

(52) U.S. Cl.
CPC .............. *C07C 43/23* (2013.01); *A61K 31/05* (2013.01); *A61K 31/11* (2013.01); *A61K 31/121* (2013.01); *C07C 43/21* (2013.01); *C07C 43/215* (2013.01); *C07C 47/277* (2013.01); *C07C 69/28* (2013.01); *C07B 2200/07* (2013.01); *C07C 2603/38* (2017.05); *C07C 2603/40* (2017.05)

(58) Field of Classification Search
CPC combination set(s) only.
See application file for complete search history.

(56) References Cited

U.S. PATENT DOCUMENTS 7,355,081 B2 4/2008 Lee et al.
2018/0037529 A1* 2/2018 Dickey .................. A61K 31/05

FOREIGN PATENT DOCUMENTS

WO WO 2012/012798 A2 1/2012

OTHER PUBLICATIONS

Kim et al. "Curcuminoids from *Curcuma longa* L. (Zingiberaceae) that protect PC12 rat pheochromocytoma and normal human umbilical vein endothelial cells from βA(1-42) insult" Neurosci. Lett. 2001, 303, 57-61. (Year: 2001).*
International Search Report in International Application No. PCT/US2013/035628, filed Apr. 8, 2013.
Tao, J. et al., Inhibitors of Nitric Oxide Production from the Bark of *Myrica rubra*: Structures of New Biphenyl Type Diarylheptanoid Glycosides and Taraxerane Type Triterpene, Bioorganic & Medicinal Chemistry, 2002, vol. 10:4005-4012, 2002 Elsevier Science Ltd.
Jones, J. R. et al., The Diarylheptanoid (+)-aR, 11S-Myricanol and Two Flavones from Bayberry (*Myrica cerifera*) Destabilize the Microtubule Associated Protein Tau, J. Nat. Prod. 2011, 74:38-44, 2011 American Chemical Society and American Society of Pharmacognosy.
Matsuda, H. et al., Bioactive Constituents of Chinese Natural Medicines. VII. [1)] Inhibitors of Degranulation in RBL-2H3 Cells and Absolute Stereostructures of Three New Diarylheptanoid Glycosides from the Bark of *Myrica rubra*, Chem. Pharm. Bull., 2002, 50(2):208-215, 2002 Pharmaceutical Society of Japan.
Ohtsu, H. et al., Antitumor Agents. 217. Curcumin Analogues as Novel Androgen Receptor Antagonists with Potential as Anti-Prostate Cancer Agents, J. Med. Chem., 2002, 45:5037-5042, 2002 American Chemical Society.

* cited by examiner

*Primary Examiner* — Amanda L Aguirre
(74) *Attorney, Agent, or Firm* — Saliwanchik, Lloyd & Eisenschenk

(57) ABSTRACT

The subject invention pertains to myricanol derivatives, therapeutic compositions, and methods for treatment of neurodegenerative diseases, in particular, neurodegenerative diseases associated with abnormal accumulation of protein tau.

8 Claims, No Drawings
Specification includes a Sequence Listing.

MYRICANOL DERIVATIVES AND USES THEREOF FOR TREATMENT OF NEURODEGENERATIVE DISEASES

CROSS-REFERENCE TO RELATED APPLICATIONS

This application is a divisional of U.S. application Ser. No. 15/414,242, filed Jan. 24, 2017; which is a continuation of U.S. application Ser. No. 14/390,960, filed Oct. 6, 2014, now U.S. Pat. No. 9,598,338, issued Mar. 21, 2017; which is the U.S. national stage application of International Patent Application No. PCT/US2013/035628, filed Apr. 8, 2013; which claims the benefit of U.S. provisional application Ser. No. 61/621,278, filed Apr. 6, 2012; and 61/678,409, filed Aug. 1, 2012; which are herein incorporated by reference in their entirety.

BACKGROUND OF THE INVENTION

Intracellular aggregation of abnormal species of phosphorylated tau (protein tau) is a major pathologic feature of a family of neurodegenerative diseases collectively referred to as the tauopathies. Tau normally functions to stabilize microtubules in neurons; however, it pathologically aggregates more than 15 neurodegenerative diseases, including Alzheimer's disease (AD) and Parkinson's disease. The most common tauopathy is Alzheimer's disease, in which paired helical filaments (PHFs) of mis-folded protein tau aggregates in neurofibrillary tangles, in dystrophic neuritis of senile plaques, and in cell processes in the neuropil. Abnormal accumulation of protein tau is closely linked with postsymptomatic progression in Alzheimer's disease. Abnormal accumulation of protein tau in the cytoplasm of neuronal and glial cells also represents major structural hallmarks in the pathology of Pick's disease, corticobasal degeneration, and progressive supranuclear palsy.

At present, researchers on the development of therapeutics for tauopathies focus primarily on agents that prevent abnormal phosphorylation or aggregation of tau proteins. However, it has been discovered that while aggregation of hyperphosphorylated protein tau is visible evidence of tauopathies, these neurofibrillary tangles appear to be less toxic than soluble intermediates of protein tau. High levels of tau intermediates, particularly aberrant tau species failed to be cleared from cells, cause cognitive dysfunction in AD and tauopathies. Therefore, agents that degrade or destabilize tau intermediates, clear aberrant tau species from cells, or otherwise reduce intracellular tau levels, are promising therapeutics for AD and tauopathies.

Existing therapeutics for the treatment tauopathies (such as AD) only demonstrate limited efficacy. Additional therapeutics for the treatment of tauopathies are needed.

BRIEF SUMMARY OF THE INVENTION

The subject invention provides myricanol derivatives for treating neurodegenerative diseases, in particular, neurodegenerative diseases associated with abnormal accumulation of protein tau.

In certain specific embodiments, the subject invention provides myricanol derivatives for treating neurodegenerative diseases, wherein the myricanol derivatives are selected from Compound 22 and Compound 23:

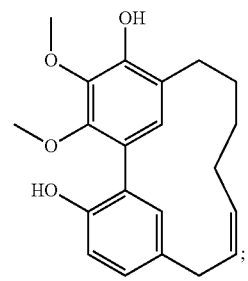
(Compound 22)

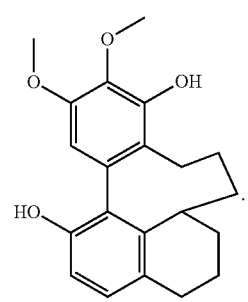
(Compound 23)

BRIEF DESCRIPTION OF THE SEQUENCES

SEQ ID NO:1 is an amino acid sequence of a tau protein isoform (tau 352) useful according to the subject invention.

SEQ ID NO:2 is an amino acid sequence of a tau protein isoform (tau 441) useful according to the subject invention.

SEQ ID NO:3 is an amino acid sequence of a tau protein isoform (tau 383) useful according to the subject invention.

SEQ ID NO:4 is an amino acid sequence of a tau protein isoform (tau 758) useful according to the subject invention.

SEQ ID NO:5 is an amino acid sequence of a tau protein isoform (tau 776) useful according to the subject invention.

SEQ ID NO:6 is an amino acid sequence of a tau protein isoform (tau 412) useful according to the subject invention.

DETAILED DESCRIPTION

The subject invention provides myricanol derivatives for treating neurodegenerative diseases, in particular, neurodegenerative diseases associated with abnormal accumulation of protein tau.

Compounds

In certain embodiments, the subject invention provides compounds 1-34, or salts thereof (as shown in Table 1).

| Compound | Structure | Molecular Weight | Name/ sample names | Results |
|---|---|---|---|---|
| 1 | 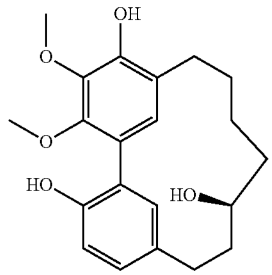 [SMILES: COc1c2cc(c(O)c1OC)CCCC[C@H](O)CCc1ccc(O)c-2c1] | 358.4281 | Myricanol/ Myr-R-1-G/ BBtol-F/ BBtol-F-E | moderate activity |
| 2 | 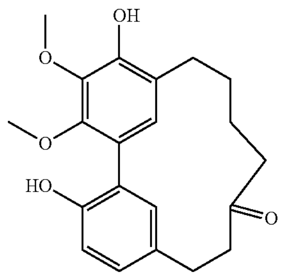 [SMILES: COc1c2cc(c(O)c1OC)CCCCC(=O)CCc1ccc(O)c-2c1] | 356.4123 | myricanone | |
| 3 | 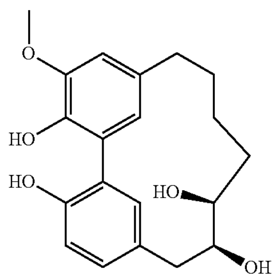 [SMILES: COc1cc2cc(c1O)-c1cc(ccc1O)C[C@H](O)[C@@H](O)CCCC2] | 344.4016 | Myricananin A | |
| 4 | 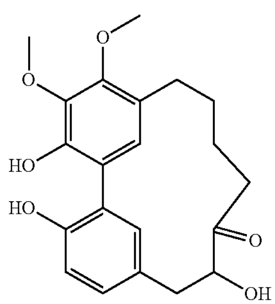 [SMILES: COc1c2cc(c(O)c1OC)-c1cc(ccc1O)CC(O)C(=O)CCCC2] | 372.4117 | Porson | |
| 5 | 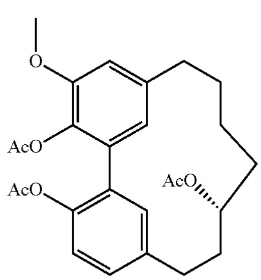 [SMILES: COc1cc2cc(c1OC(C)=O)-c1cc(ccc1OC(C)=O)CC[C@H](OC(C)=O)CCCC2] | 454.5122 | Myricanol triacetate | |

-continued

| Compound | Structure | Molecular Weight | Name/ sample names | Results |
|---|---|---|---|---|
| 6 | 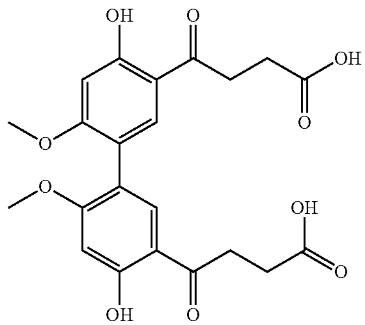 [SMILES: COc1cc(O)c(C(=O)CCC(=O)O)cc1-c1cc(C(=O)CCC(=O)O)c(O)cc1OC] | 446.4041 | 4-[5'-(3-carboxypropanoyl)-4,4'-dihydroxy-2',6-dimethoxy[1,1'-biphenyl]-3-yl]-4-oxobutanoic acid | |
| 7 | 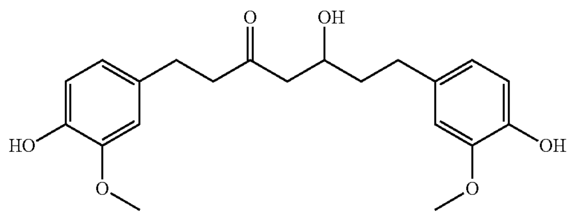 [SMILES: COc1cc(CCC(=O)CC(O)CCc2ccc(O)c(OC)c2)ccc1O] | 374.4275 | Hexahydrocurcumin | |
| 8 | 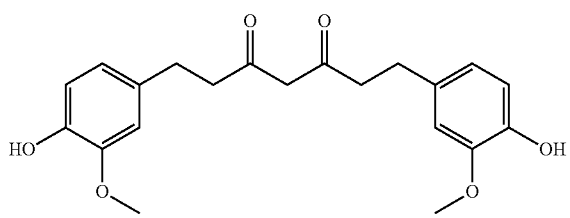 [SMILES: COc1cc(CCC(=O)CC(=O)CCc2ccc(O)c(OC)c2)ccc1O] | 372.4117 | Tetrahydrocurcumin | |
| 9 | 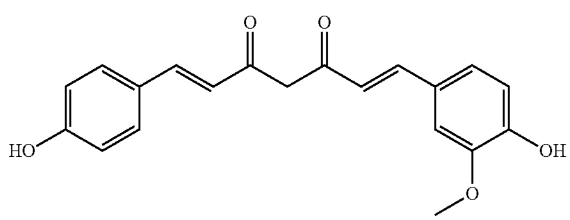 [SMILES: COc1cc(/C=C/C(=O)CC(=O)/C=C/c2ccc(O)cc2)ccc1O] | 338.3539 | Demethoxycurcumin | active |
| 10 | 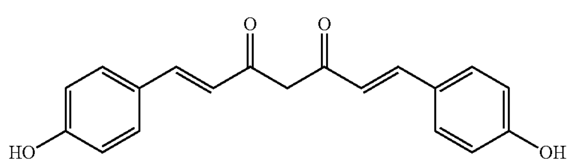 [SMILES: O=C(/C=C/c1ccc(O)cc1)CC(=O)/C=C/c1ccc(O)cc1] | 308.3279 | Bisdemethoxycurcumin | active |
| 11 | 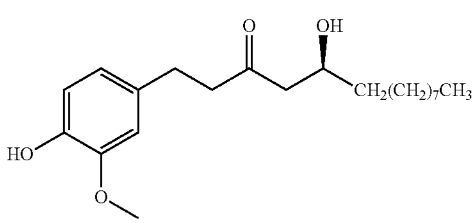 | 350.4923 | [10]-Gingerol | Active |
| 12 | 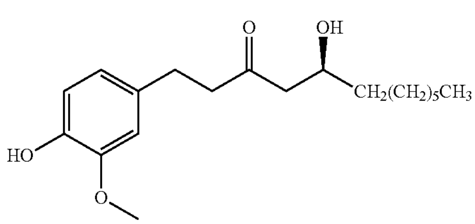 | 322.4391 | [8]-Gingerol | |

-continued
| Compound | Structure | Molecular Weight | Name/ sample names | Results |
|---|---|---|---|---|
| 13 | 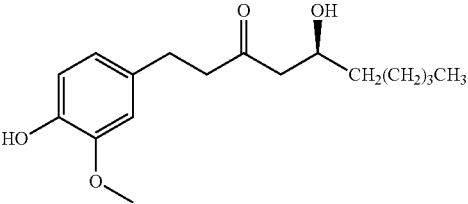 | 294.3859 | [6]-Gingerol | |
| 14 | 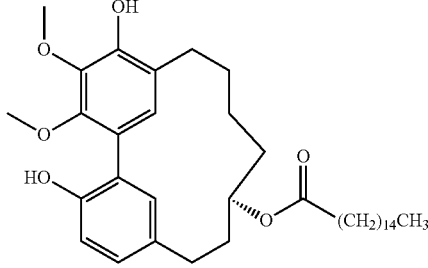 | 596.8369 | Myricanol 11-monopalmitate/ Myr-R-1-E | |
| 15 | 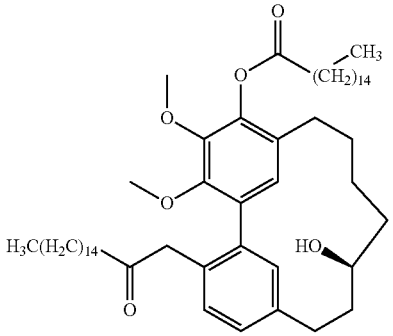 | 833.2729 | Myricanol 11,17-dipalmitate/ Myr-R-3-E-4 | |
| 16 | 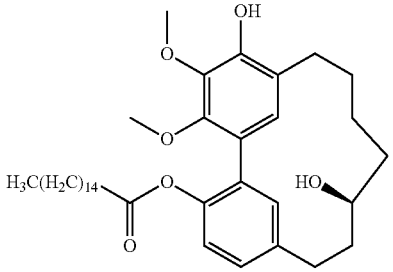 | 596.8369 | myricanol 17-palmitate/ Myr-R-3-F | |
| 17 | 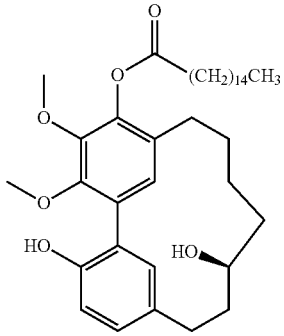 | 596.8369 | myricanol 5-palmitate/ Myr-R-3-E-2 | |

-continued

| Compound | Structure | Molecular Weight | Name/ sample names | Results |
|---|---|---|---|---|
| 18 | 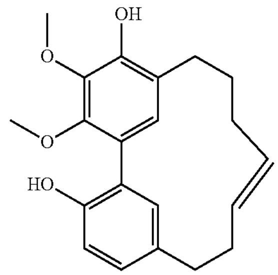 [SMILES: COc1c2cc(c(O)c1OC)CCC/C=C/CCc1ccc(O)c-2c1] | 340.4129 | Myricacene A (trans)/ Myr-R-9-4; Myr-16-13-4 | active |
| 19 | 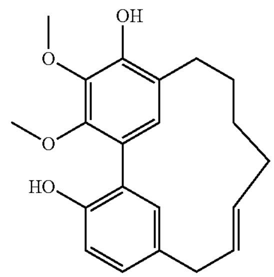 [SMILES: COc1c2cc(c(O)c1OC)CCCC/C=C/Cc1ccc(O)c-2c1] | 340.4129 | Myricacene B (trans)/ Myr-R-9-2-8; Myr-R-16-15 | active |
| 20 | 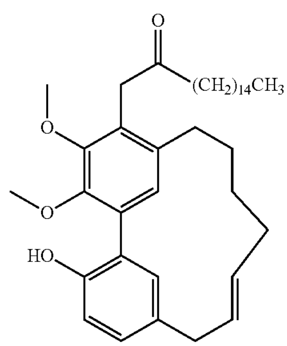 | 576.8488 | Myricacene B (trans) 5-palmitate/ Myr-R20-2 | |
| 21 | 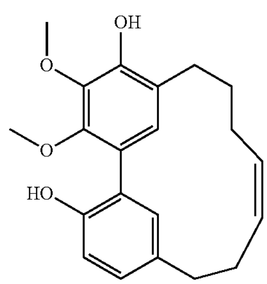 [SMILES: COc1c2cc(c(O)c1OC)CCC/C=C\CCc1ccc(O)c-2c1] | 340.4129 | Myricacene A (cis)/ Myr-R-9-2-4; Myr-R-16-13-2 | moderately active |
| 22 | 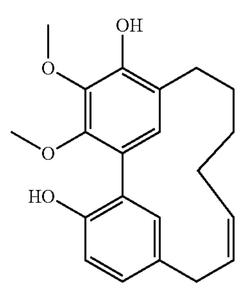 [SMILES: COc1c2cc(c(O)c1OC)CCCC/C=C\Cc1ccc(O)c-2c1] | 340.4129 | Myricacene B (cis)/ Myr-R-9-2-6 | active |

-continued

| Compound | Structure | Molecular Weight | Name/ sample names | Results |
|---|---|---|---|---|
| 23 | 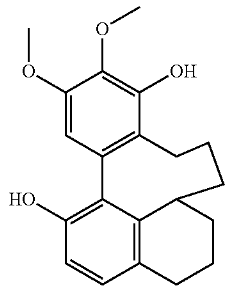 [SMILES: COc1cc2c(c(O)c1OC)CCCC1CCCc3ccc(O)c-2c31] | 340.4129 | Myr-R-16-6 | very active |
| 24 | 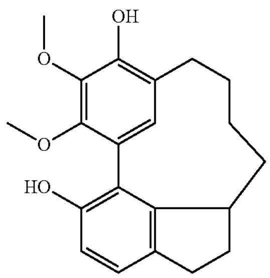 [SMILES: COc1c2cc(c(O)c1OC)CCCCC1CCc3ccc(O)c-2c31] | 340.4129 | Myr-R-16-4-2 | active |
| 25 | 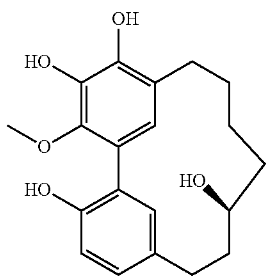 [SMILES: COc1c2cc(c(O)c1O)CCCC[C@H](O)CCc1ccc(O)c-2c1] | 344.4016 | Myr-R-21-4-2 | |
| 26 | 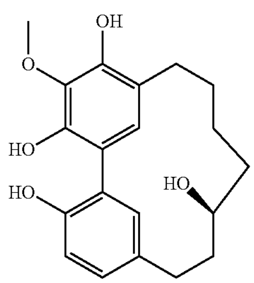 [SMILES: COc1c(O)c2cc(c1O)-c1cc(ccc1O)CC[C@@H](O)CCCC2] | 344.4016 | Myr-R-21-4-4 | |
| 27 | 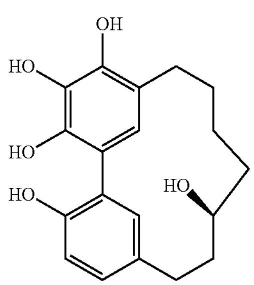 [SMILES: Oc1ccc2cc1-c1cc(c(O)c(O)c1O)CCCC[C@H](O)CC2] | 330.3750 | Myr-R-21-2 | |

-continued

| Compound | Structure | Molecular Weight | Name/ sample names | Results |
|---|---|---|---|---|
| 28 | 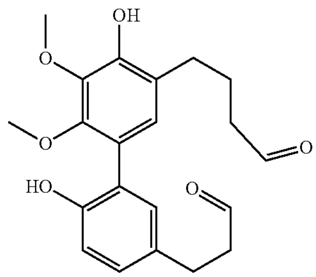 [SMILES: COc1c(-c2cc(CCC=O)ccc2O)cc(CCCC=O)c(O)c1OC] | 372.4117 | Myr-R-25-2/ Myr-R-26-2 | |
| 29 | 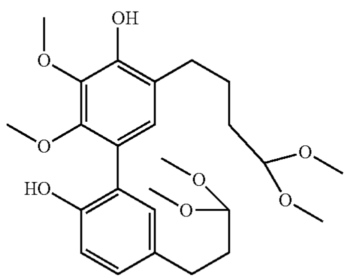 | 464.5485 | Myr-R-25-8 | |
| 30 | 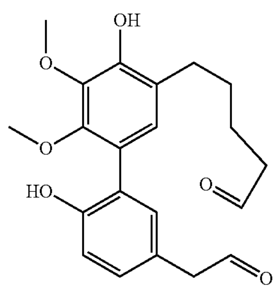 [SMILES: COc1c(-c2cc(CC=O)ccc2O)cc(CCCCC=O)c(O)c1OC] | 372.4117 | Myr-R-27-2 | |
| 31 | 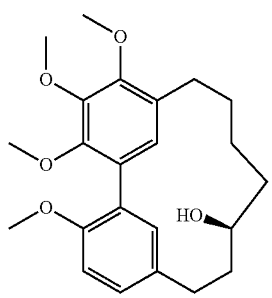 [SMILES: COc1ccc2cc1-c1cc(c(OC)c(OC)c1OC)CCCC[C@H](O)CC2] | 386.4813 | Dimethylmyricanol/ Myr-R-31 | |
| 32 | 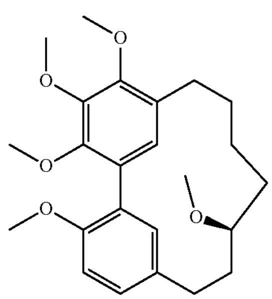 [SMILES: COc1ccc2cc1-c1cc(c(OC)c(OC)c1OC)CCCC[C@H](OC)CC2] | 400.5079 | Trimethylmyricanol/ Myr-R-33-4 | |

-continued

| Compound | Structure | Molecular Weight | Name/ sample names | Results |
|---|---|---|---|---|
| 33 | 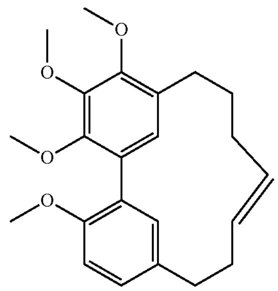 [SMILES: COc1ccc2cc1-c1cc(c(OC)c(OC)c1OC)CCC/C=C/CC2] | 368.4660 | Dimethylmyricacene/ Myr-R-32-2 | |
| 34 | 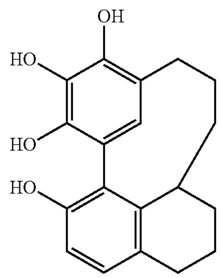 [SMILES: Oc1ccc2c3c1-c1cc(c(O)c(O)c1O)CCCC3CCC2] | 312.3597 | Myr-R30-2 | |

In certain embodiments, the subject invention pertains to the uses of Compound 9, Compound 10, Compound 11, Compound 18, Compound 19, Compound 21, Compound 22, Compound 23, and Compound 24, and salts thereof, for treating neurodegenerative diseases, in particular, neurodegenerative diseases associated with abnormal accumulation of protein tau.

In certain specific embodiments, the subject invention pertains to the uses of compounds 22 and 23, or salts thereof, for treating neurodegenerative diseases, in particular, neurodegenerative diseases associated with abnormal accumulation of protein tau.

In one embodiment, the subject invention provides an isolated or substantially pure compound of formula A, or a salt thereof,

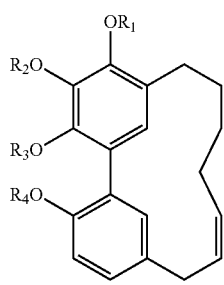

(A)

wherein $R_1$-$R_4$ are, independently, —H or any group that forms an ester or ether bond.

In one embodiment, the subject invention provides an isolated or substantially pure compound of formula B, or a salt thereof,

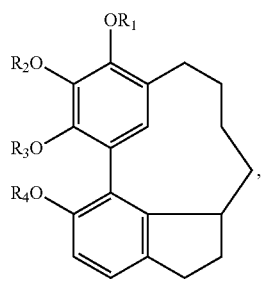

(B)

wherein $R_1$-$R_4$ are, independently, —H or any group that forms an ester or ether bond.

In one embodiment, the subject invention provides an isolated or substantially pure compound of formula C, or a salt thereof, (C)

wherein $R_1$-$R_4$ are, independently, —H or any group that forms an ester or ether bond.

In one embodiment, the subject invention provides an isolated or substantially pure compound of formula D, or a salt thereof,

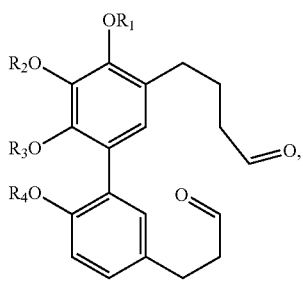
(D)

wherein $R_1$-$R_4$ are, independently, —H or any group that forms an ester or ether bond.

In one embodiment, the subject invention provides an isolated or substantially pure compound of formula E, or a salt thereof,

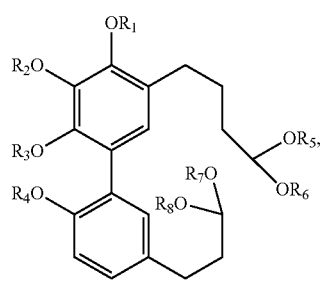
(E)

wherein $R_1$-$R_8$ are, independently, —H or any group that forms an ester or ether bond.

In one embodiment, the subject invention provides an isolated or substantially pure compound of formula F, or a salt thereof,

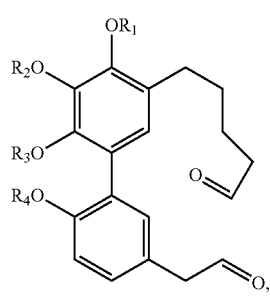
(F)

wherein $R_1$-$R_4$ are, independently, —H or any group that forms an ester or ether bond.

In one embodiment, the subject invention provides an isolated or substantially pure compound of formula G, or a salt thereof,

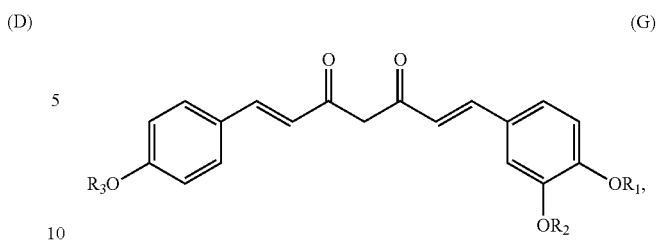
(G)

wherein $R_1$-$R_3$ are, independently, —H or any group that forms an ester or ether bond.

In one embodiment, the subject invention provides an isolated or substantially pure compound of formula H, or a salt thereof,

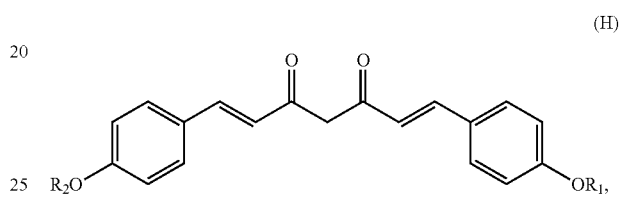
(H)

wherein $R_1$ and $R_2$ are, independently, —H or any group that forms an ester or ether bond.

In one embodiment, the subject invention provides an isolated or substantially pure compound of formula I, or a salt thereof,

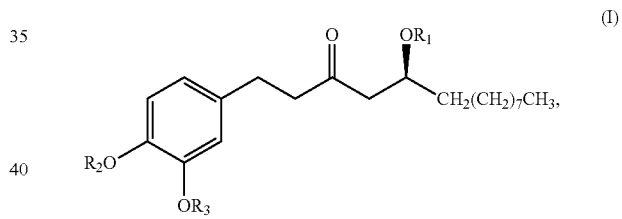
(I)

wherein $R_1$-$R_3$ are, independently, —H or any group that forms an ester or ether bond.

In one embodiment, the subject invention provides an isolated or substantially pure compound of formula J, or a salt thereof,

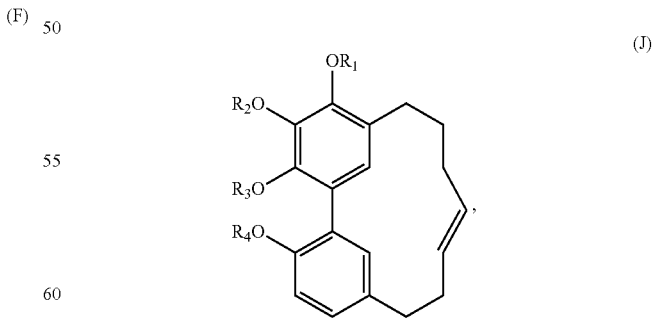
(J)

wherein $R_1$-$R_4$ are, independently, —H or any group that forms an ester or ether bond.

In one embodiment, the subject invention provides an isolated or substantially pure compound of formula K, or a salt thereof,

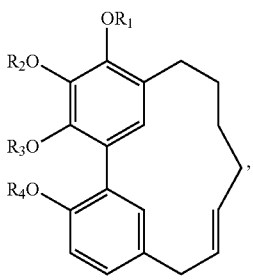

(K)

wherein R$_1$-R$_4$ are, independently, —H or any group that forms an ester or ether bond.

In one embodiment, the subject invention provides an isolated or substantially pure compound of formula L, or a salt thereof,

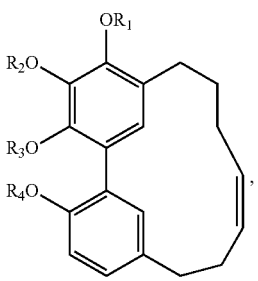

(L)

wherein R$_1$-R$_4$ are, independently, —H or any group that forms an ester or ether bond.

In certain embodiments, one or more of R$_1$-R$_8$ of formula A or formula L can be, —H, unsubstituted or substituted alkyl, alkenyl, —COOH, acyl, benzyl, or cyclic alkyl. In certain embodiments, any or all of R$_1$-R$_8$ have fewer than 6 carbon atoms.

In certain embodiments, one or more of R$_1$-R$_8$ of formula A or formula L can be an organic or inorganic acid group including, but not limited to, acetic acid, carboxylic acid, aspartic acid, formic acid, citric acid, benzoic acid, hippuric acid, malic acid, mucic acid, phosphoric acid, sulfuric acid, gluconic acid, maleic acid, succinic acid, tartaric acid, and lactic acid.

In certain embodiments, one or more of R$_1$-R$_8$ of formula A or formula L can be a carbohydrate moiety, in which a monosaccharide, disaccharide, oligosaccharide, or its derivative loses an —H in its hydroxyl group and thereby forms a radical. Suitable carbohydrate moieties can be derived, for example, from glucose, fructose, and sucrose.

The compounds of the present invention can be synthesized. In preferred embodiments, the compounds of the present invention are at least 75% pure, preferably at least 90% pure, more preferably are more than 95% pure, and most preferably are more than 99% pure (substantially pure).

As used herein, "isolated" refers to compounds that have been removed from any environment in which they may exist in nature.

The present invention further embodies stereoisomers of the compounds of formula A or formula L. The term "stereoisomer" encompasses all enantiomerically/stereomerically pure and enantiomerically/stereomerically enriched compounds disclosed herein.

The enantiomeric forms of the compounds (e.g., isolated or chemically synthesized) of the invention are substantially free from one another (i.e., in enantiomeric excess). In other words, the "+" forms of the compounds are substantially free from the "−" forms of the compounds. Conversely, "−" forms of the compounds are substantially free of "+" forms of the compounds. In one embodiment of the invention, the enantiomeric compounds are in at least about 80% of the "+" forms. In a preferred embodiment, the compounds are in at least about 90% of the "+" forms. In a more preferred embodiment, the compounds are in at least about 95% of the "+" forms. In an even more preferred embodiment, the compounds are in at least about 97.5% of the "+" forms. In a most preferred embodiment, the compounds are in at least about 99% of the "+" forms.

"Alkyl" means a linear saturated monovalent radical of one to sixteen carbon atoms or a branched saturated monovalent of three to sixteen carbon atoms. It may include hydrocarbon radicals of one to four or one to three carbon atoms, which may be linear. Examples include methyl, ethyl, propyl, 2-propyl, n-butyl, iso-butyl, tert-butyl, pentyl, and the like.

"Alkenyl" means a linear or branched C$_2$-C$_{16}$ hydrocarbon radical that comprises one or more carbon-carbon double bonds. Examples include propylenyl, buten-1-yl, isobutenyl, penten-1-yl, 2,2-methylbuten-1-yl, 3-methylbuten-1-yl, hexan-1-yl, hepten-1-yl, octen-1-yl, and the like.

"Acyl" means a radical —C(O)R where R is hydrogen, alkyl or cycloalkyl, or heterocycloalkyl. Examples include formyl, acetyl, ethylcarbonyl, and the like.

"Carboxyl" means the radical —C(O)OH.

"Halo" means fluoro, chloro, bromo or iodo.

"Haloalkyl" means alkyl substituted with one or more same or different halo atoms, e.g., —CH$_2$Cl, —CH$_2$Br, —CF$_3$, —CH$_2$CH$_2$Cl, —CH$_2$CCl$_3$, and the like.

"Hydroxy" means the radical —OH.

"Hydroxyalkyl" means an alkyl radical as defined herein, substituted with one or more, preferably one, two or three hydroxy groups. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxy-propyl, preferably 2-hydroxyethyl, 2,3-dihydroxypropyl and 1-(hydroxymethyl) 2-hydroxyethyl.

"Substituted," as used herein, refers to a compound or chemical moiety in which at least one hydrogen atom of that compound or chemical moiety is replaced with a second chemical moiety. In certain embodiments, substituents include, but are not limited to, halogen; alkyl; heteroalkyl; alkenyl; alkynyl; hydroxyl, aryl, hydroxyalkyl, heteroaryl, hydroxy; alkoxyl; amino; nitro; thiol; carbocyclic cycloalkyl, amino (primary, secondary or tertiary); o-lower alkyl; o-aryl, aryl; aryl-lower alkyl.

In one embodiment, the subject invention pertains to the therapeutic use of Compound 22, Compound 23, and Compound 24:

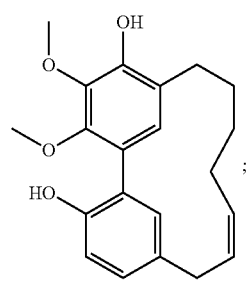

(Compound 22)

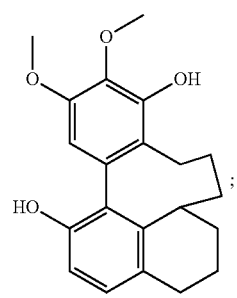

(Compound 23)

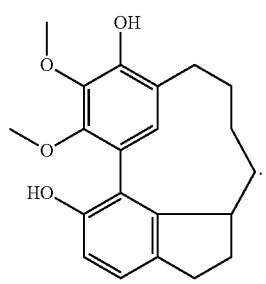

(Compound 24)

Treatment of Neurodegenerative Diseases

The compounds and compositions of the subject invention, through administration to a subject, are useful for treating or ameliorating neurodegenerative diseases or conditions, in particular, neurodegenerative diseases or conditions associated with abnormally high levels of protein tau and/or abnormal accumulation of protein tau in neurons. In a preferred embodiment, the compounds and compositions of the subject invention are useful to treat or ameliorate Alzheimer's disease or Parkinson's disease.

In one embodiment, the subject invention provides a method for treating a neurodegenerative disease or condition, particularly a disease or condition associated with abnormally high levels of protein tau and/or abnormal accumulation of protein tau in neurons, wherein the method comprises administering, to a subject in need of such treatment, an effective amount of a composition comprising a compound selected from Compound 9, Compound 10, Compound 11, Compound 18, Compound 19, Compound 21, Compound 22, Compound 23, and Compound 24, or a salt thereof.

In one embodiment, the subject invention provides a method for treating a neurodegenerative disease or condition, particularly a disease or condition associated with abnormally high levels of protein tau and/or abnormal accumulation of protein tau in neurons, wherein the method comprises administering, to a subject in need of such treatment, an effective amount of a composition comprising a compound selected from any of formula A or formula L, or a salt thereof.

In one embodiment, the subject invention provides a method of reducing intracellular tau levels, wherein said method comprises administering, to cells comprising protein tau, an effective amount of a compound of formula A to formula L.

In one embodiment, the following isomer of Compound 23 is administered to a subject having a neurodegenerative disease or condition, particularly a disease or condition associated with abnormally high levels of protein tau and/or abnormal accumulation of protein tau in neurons,

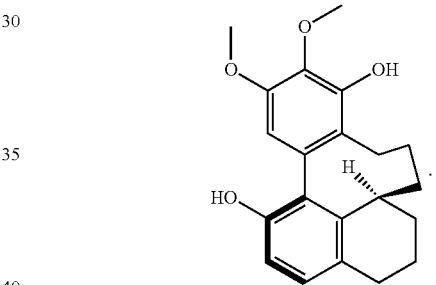

The term "subject," as used herein, describes an organism, including mammals such as primates, to which treatment with the compositions according to the subject invention can be administered. Mammalian species that can benefit from the disclosed methods of treatment include, but are not limited to, apes, chimpanzees, orangutans, humans, monkeys; and other animals such as dogs, cats, horses, cattle, pigs, sheep, goats, chickens, mice, rats, guinea pigs, and hamsters. Typically, the subject is a human.

The term "tau protein" or any grammatical variation thereof (e.g., protein tau and tau etc.), as used herein, refers generally to any protein of the microtubule-associated tau protein family. Members of the tau family share the common features of a characteristic N-terminal segment, sequences of approximately 50 amino acids inserted in the N-terminal segment, a characteristic tandem repeat region consisting of 3 or 4 tandem repeats of 31-32 amino acids, and a C-terminal tail. Tau proteins of the subject invention may be in a form of soluble tau intermediates, functional, aberrant, abnormally-truncated, mis-folded or mis-processed tau, and phosphorylated tau.

Preferably, tau protein of the subject invention is of mammalian origin, more preferably, of human origin. Specifically, tau proteins of the subject invention include microtubule-associated protein translated from the human chromosomal sequence of GenBank Accession No. AH005895

In one embodiment, the subject invention pertains to the therapeutic use of the following isomer of Compound 23:

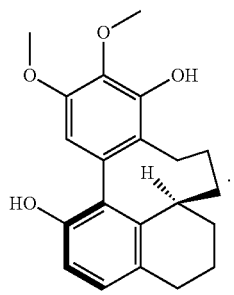

and naturally-occurring mammalian variants or isoforms thereof. Six human brain tau isoforms are currently known, including tau352 (GenBank Accession No. NP_058525) (SEQ ID NO:1), tau441 (GenBank Accession No. NP_005901) (SEQ ID NO:2), tau383 (GenBank Accession No. NP_058518) (SEQ ID NO:3), tau758 (GenBank Accession No. NP_058519) (SEQ ID NO:4), tau776 (GenBank Accession No. NP_001116538) (SEQ ID NO:5), and tau412 (GenBank Accession No. NP_001116539) (SEQ ID NO:6).

The term "treatment" or any grammatical variation thereof (e.g., treat, treating and treatment etc.), as used herein, includes but is not limited to, ameliorating or alleviating a symptom of a disease or condition, reducing, suppressing, inhibiting, lessening, or affecting the progression, severity, and/or scope of a condition, chance of reoccurrence or returning of a disease after a remission. For instance, the term "treatment" includes (i) ameliorating a symptom associated with a neurodegenerative disease in a patient diagnosed with the neurodegenerative disease; and/or (ii) relieving (such as attenuating the progress of) or remedying a neurodegenerative disease in a patient diagnosed with the neurodegenerative disease.

In one embodiment, the treatment method of the subject invention reduces tau levels and/or improves tau clearance. Normal, functional tau is less affected by clearance pathways in the cell than aberrant tau. In one embodiment, the treatment method of the subject invention modulates tau clearance by selectively targeting abnormal tau.

In an embodiment, the subject invention provides a method for treating or ameliorating a neurodegenerative disease or condition. The method comprises administering, to a subject in need of such treatment, an effective amount of compounds and compositions of the subject invention.

In an embodiment, the therapeutic composition is administered to a human subject who has symptoms of, or is diagnosed with, a neurodegenerative disease. In preferred embodiments, the therapeutic composition is administered to a human subject who has symptoms of, or is diagnosed with, a neurodegenerative disease associated with abnormal accumulation of protein tau. For instance, the therapeutic composition is administered to a human subject who has elevated levels of soluble protein tau and/or hyperphosphorylated protein tau in the nervous system, such as in the brain or cytoplasm of neuronal and glial cells. In addition, the therapeutic composition is administered to a human subject who exhibits pathologic features such as neurofibrillary tangles or senile plaques in neuronal cells and/or cell processes. In a specific embodiment, the therapeutic composition is administered to a human subject who has symptoms of, or is diagnosed with, Alzheimer's disease.

The identification of subjects who are in need of treatment for a neurodegenerative disease is well within the knowledge and ability of one skilled in the art. By way of example, a clinician skilled in the art can readily identify, by the use of clinical tests, neurologic and physical examination, and medical/family history, those patients who are suffering from a neurodegenerative disease as well as those who are predisposed to developing a neurodegenerative disease and thus readily determine if an individual is in need of treatment of the subject invention. For instance, neurofibrillary tangles or senile plaques present in neuronal cells and/or cell processes can be determined using electron microscopy (EM) or other clinical techniques known in the art. In addition, spinal fluid or cerebral fluid samples or tissues samples from hippocampal tissue or frontal cortex tissue samples may be obtained from a subject and levels of protein tau present in the samples can be determined using routine techniques such as enzyme-linked immunosorbant assay (ELISA), western blot, and immunological assays.

The term "effective amount" or "therapeutically effective amount," as used herein, refers to an amount that is capable of preventing, treating or ameliorating a disease or condition or otherwise capable of producing an intended therapeutic effect. For instance, the effective amount of the compounds and compositions of the subject invention is an amount capable of reducing levels of protein tau in a subject. In certain embodiments, the effective amount enables a 5%, 25%, 50%, 75%, 90%, 95%, 99% and 100% reduction of levels of protein tau (e.g. soluble protein tau intermediates and/or aberrant protein tau) in a subject.

The compounds and compositions of the subject invention can be used to treat or ameliorate neurodegenerative diseases including, but not limited to, Alzheimer's disease, Parkinson's disease, Amyotrophic lateral sclerosis (ALS), Huntington's disease, multiple sclerosis, Pick's disease, fronto temporal dementia, cortico-basal degeneration, progressive supranuclear palsy, Creutzfeldt-Jakob disease, Gerstmann-Straussler-Scheinker syndrome, and Kuru.

The compounds and compositions of the subject invention can also be used to treat or ameliorate neurodegenerative diseases including, but not limited to, Down's syndrome, Argyrophilic grain disease, parkinsonism dementia complex of Guam, non-Guamanian motor neurone disease with NFT, Niemann-Pick disease type C, subacute sclerosing panencephalitis, postencephalitic parkinsonism, dementia pugilistica, myotonic dystrophy, prion protein amyloid antipathy, and Hallervorden-Spatz disease.

The compounds and compositions of the subject invention are particularly useful to treat or ameliorate a neurodegenerative disease involving tau pathologies (i.e., tauopathies) including, but not limited to, Alzheimer's disease, Parkinson's disease, frontotemporal dementia, frontotemporal dementia with Parkinsonism, frontotemporal lobe dementia, pallidopontonigral degeneration, progressive supranuclear palsy, multiple system tauopathy, multiple system tauopathy with presenile dementia, Wilhelmsen-Lynch disease, Pick's disease, and Pick's disease-like dementia.

Specifically, the compounds and compositions of the subject invention are particularly useful to treat or ameliorate a disease or condition arising, at least in part, from abnormally high levels of protein tau in the nervous system, such as in cytoplasm of neuronal and glial cells and in neuronal and glial cell processes. Thus, the subject invention is particularly useful for treatment of neurodegenerative diseases and disorders, in which reduction of levels of protein tau in the nervous system would be beneficial.

In addition, the compounds and compositions of the subject invention are useful for alleviating or attenuating symptoms arising from or associated with neurodegenerative diseases, including cognitive dysfunction, impaired memory, impaired mental capacities, emotional disturbances, speech dysfunction, incontinence, tremor, postural instability, rigidity or stiff movement, muscle paralysis, and pain.

Therapeutic Compositions and Formulations

The subject invention further provides therapeutic compositions that contain a therapeutically effective amount of the compounds and compositions and a pharmaceutically acceptable carrier or adjuvant.

The terms "pharmaceutically acceptable", "physiologically tolerable" and grammatical variations thereof, as used herein, include compositions, carriers, diluents and reagents, are used interchangeably, and represent that the materials are capable of administration to or upon a subject such as mammal.

The term "carrier" refers to an adjuvant, excipient, or vehicle with which the compound is administered. Such pharmaceutical carriers can be sterile liquids, such as water and oils, including those of petroleum oil such as mineral oil, vegetable oil such as peanut oil, soybean oil, and sesame oil, animal oil, or oil of synthetic origin. Particularly preferred pharmaceutical carriers for treatment of or amelioration of a neurodegenerative disease are carriers that can penetrate the blood/brain barrier.

Suitable carriers also include ethanol, dimethyl sulfoxide, glycerol, silica, alumina, starch, sorbitol, inosital, xylitol, D-xylose, mannitol, powdered cellulose, microcrystalline cellulose, talc, colloidal silicon dioxide, calcium carbonate, calcium phosphate, calcium aluminium silicate, aluminium hydroxide, sodium starch phosphate, lecithin, and equivalent carriers and diluents. Saline solutions and aqueous dextrose and glycerol solutions can also be employed as liquid carriers, particularly for injectable solutions.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The therapeutic composition, if desired, can also contain minor amounts of wetting or emulsifying agents, or pH buffering agents.

The amount of active ingredient that may be combined with the carrier materials to produce a single dosage form will vary, depending on the type of the condition and the subject to be treated. In general, a therapeutic composition contains from about 5% to about 95% active ingredient (w/w). More specifically, a therapeutic composition contains from about 20% (w/w) to about 80% or about 30% to about 70% active ingredient (w/w).

The compounds and compositions of the subject invention can be formulated according to known methods for preparing pharmaceutically useful compositions. Formulations are described in detail in a number of sources which are well known and readily available to those skilled in the art. For example, Remington's Pharmaceutical Science by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

The therapeutic or pharmaceutical compositions of the subject invention can also be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The preparation of a pharmacological composition that contains active ingredients dissolved or dispersed therein is well understood in the art and need not be limited based on formulation. Typically such compositions are prepared as injectables either as liquid solutions or suspensions; however, solid forms suitable for solution, or suspensions, in liquid prior to use also can be prepared. The preparation also can be emulsified, such as oil-in-water emulsion.

The compounds and compositions of the subject invention in prescription amounts can be readily made into any form of drug, suitable for administering to humans or animals. Suitable forms include, for example, tinctures, decoctions, and dry extracts. These can be taken orally, applied through venous injection mucous membranes or inhalation. The active ingredient can also be formulated into capsules, powder, pallets, pastille, suppositories, oral solutions, pasteurized gastroenteric suspension injections, small or large amounts of injection, frozen powder injections, pasteurized powder injections and the like.

Routes of Administration

The compounds and compositions of the subject invention can be administered to the subject being treated by standard routes, including oral, inhalation, or parenteral administration including intravenous, subcutaneous, topical, transdermal, intradermal, transmucosal, intraperitoneal, intramuscular, intracapsular, intraorbital, intracardiac, transtracheal, subcutaneous, subcuticular, intraarticular, subcapsular, subarachnoid, intraspinal, epidural and intrasternal injection, infusion, and electroporation, as well as co-administration as a component of any medical device or object to be inserted (temporarily or permanently) into a subject. In a preferred embodiment, the compounds and compositions of the subject invention are administered orally.

The amount of the therapeutic or pharmaceutical composition of the subject invention which is effective in the treatment of a neurodegenerative disease will depend on the nature of the disease, condition or disorder and can be determined by standard clinical techniques. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg and preferably about 1 to 100 mg/kg; intranasal instillation, 0.01 to about 20 mg/kg; and aerosol, 0.01 to about 20 mg/kg of animal (body) weight.

Once improvement of the patient's condition has occurred, a maintenance dose is administered if necessary. Subsequently, the dosage or the frequency of administration, or both, may be reduced as a function of the symptoms to a level at which the improved condition is retained. When the symptoms have been alleviated to the desired level, treatment should cease. Patients may however require intermittent treatment on a long-term basis upon any recurrence of disease symptoms.

In addition, in vitro assays may optionally be employed to help identify optimal dosage ranges. The precise dose to be employed in the formulation will also depend on the route of administration, and the seriousness of the disease, condition or disorder, and should be decided according to the judgment of the practitioner and each patient's circumstances. Effective doses may be extrapolated from dose-response curves derived from in vitro or animal model test systems.

EXAMPLE

Following is an example that illustrates procedures for practicing the invention. The example should not be construed as limiting.

Example 1—Myricanol Derivatives and Uses Thereof for Reducing Tau Protein Levels This Example shows myricanol derivatives, their synthetic schemes, and uses for reducing protein tau levels.
(+)-aR,11S-Myricanol Extraction from Bayberry Root Bark *Myrica cerifera* (Natural Frontier Co-Op)

Tau-reducing-guided fractionation study of *Myrica cerifera* (bay berry root bark) led to the identification (+)-aR, 11S-myricanol as a tau destabilizer agent with an $IC_{50}$ of 35 µM. The bayberry root-bark powder (5×1 kg) was extracted with 5×2 L of toluene under agitation in a (5×) flask protected from light (3×24 h). The filtrate was concentrated and gave 58 g of extract. The toluene extract was purified using silica gel MPLC, eluting with a gradient of 0 to 40% ethyl acetate/hexanes to yield 27 g of (+)-aR,11S-myricanol $[\alpha]_D^{21}$=48.2 (c=1.1, Chloroform).

Derivatization

Oxidation

Myricanol (120 mg) was treated in a solution of dichloromethane (10 mL) with 150 mg of pyridinium chlorochromate (PCC). After 2 h the reaction was treated into ice-water and EtOAc extraction. The organic layer was then extracted with saturated aqueous $NaHCO_3$ and brine, then dried over $MgSO_4$ powder and filtered. The residue was then purified by normal phase HPLC using an isocratic solvent mixture of 20% ethyl acetate and 80% hexane to give 20 mg of myricanone.

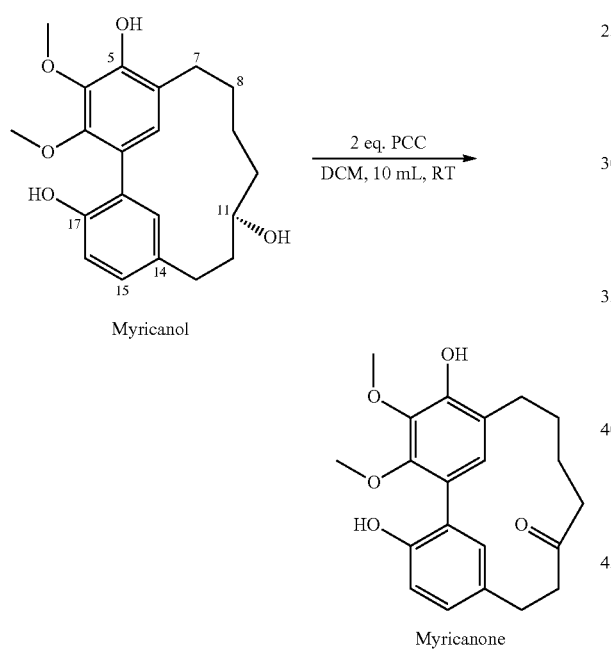

Dehydration

Myricanol (50 mg) was treated in a solution of 10 mL of toluene with 79 mg of para toluene sulfonic acid. The solution was boiled for 24 h, cooled, diluted with hexane, washed successively with saturated solutions of $NaHCO_3$ and NaCl, dried over $MgSO_4$, and evaporated. The mixture was purified by a first HPLC using normal phase column in an isocratic solvent mixture of 3% ethyl acetate/hexane. Two fractions were collected. The first eluted fraction was purified by reversed phase HPLC using an isocratic solvent mixture of 32% acetonitrile/water to give 5 mg of pure myricacene A (trans) material and 0.5 mg of myricacene A (cis) and 2 mg of myricacene B (trans). The second fraction was separated using the same reverse phase condition and provided 21 mg and 8 mg of the respective 6-membered-ring and 5-membered ring derivatives $[\alpha]_D^{21}$=0 (c=0.1, Chloroform).

When para toluene sulfonic acid was added at catalytic level (0.3 mg, during 72 hours) after normal and reverse phase HPLC purification: 15 mg of myricacene A (trans), 9 mg of myricacene A (trans), 4 mg of myricacene A (cis), 4 mg of myricacene B (cis), 3 mg of the 6-membered ring derivative and 3 mg of the 5-membered ring derivative.

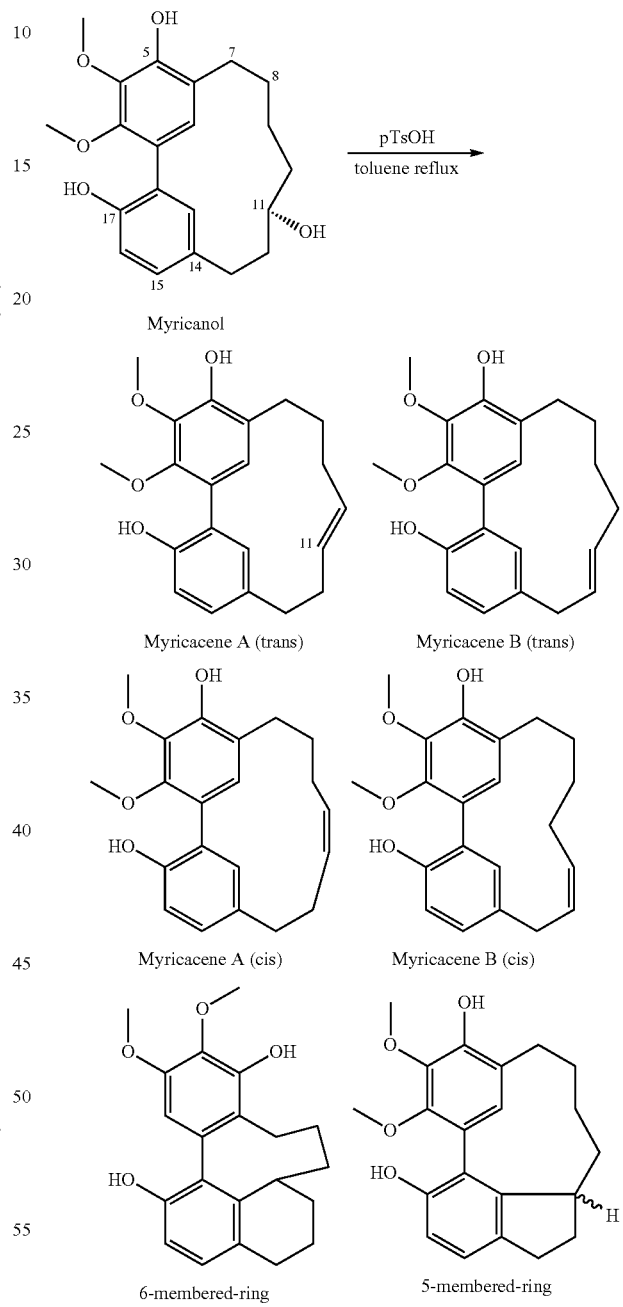

Each of the 6-membered ring and the 5-membered ring derivatives (shown above) have four possible isomers by the chiral center at position C10 and C12, respectively, and the biphenyl orientation.

During the purification process, the 6-membered ring provided crystal and the X-ray crystallographic analysis provided the relative configuration below:

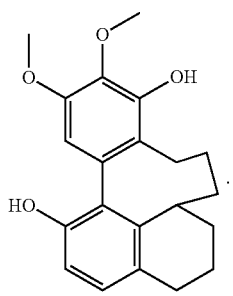

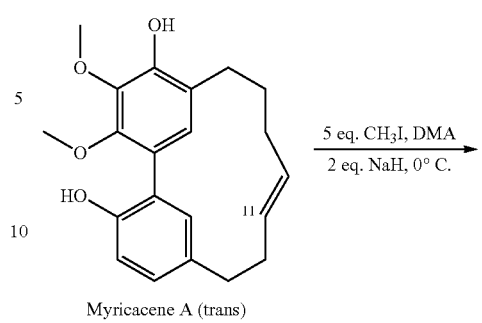

Myricacene A (trans)

Methylation

1) Sodium hydride (4 mg) was added to a solution of myricanol (20 mg) in methyl iodide (1 ml) and dimethylacetamide (DMA, 5 ml) at 0° C. for 30 min. The reaction mixture was kept for 4 h at 0° C. then diluted with water and extracted with diethyl ether. The ether extract was washed with water and brine, and was dried over sodium sulfate, filtered and evaporated. The residue was separated by normal phase HPLC using 45% ethyl acetate and 55% hexane and provided 8 mg of trimethyl myricanol and 5 mg of dimethylmyricanol.

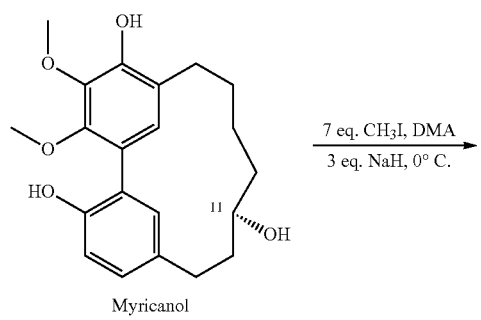

Myricanol

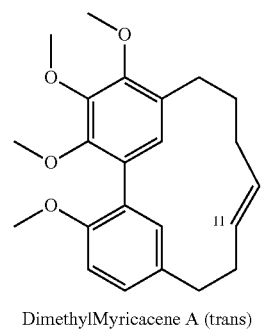

DimethylMyricacene A (trans)

Demethylation 10 mg of myricanol was mixed to 5 mL of dichloromethane (3 mL) then the resulting solution was added to solution of 5 mL dichloromethane and 0.2 mL $BBr_3$ at −10° C. and stirred under nitrogen for 1 h to room temperature. The reaction mixture was diluted with water, stirred and extracted with chloroform. The chloroform extract was washed with brine, dried over magnesium sulfate, filtered and evaporated to give after reverse phase HPLC (65% water and 35% acetonitrile) 2 mg of 3-hydroxy-myricanol, 3 mg of 4-hydroxy-miricanol and 1 mg of 3,4-dihydroxy-myricanol.

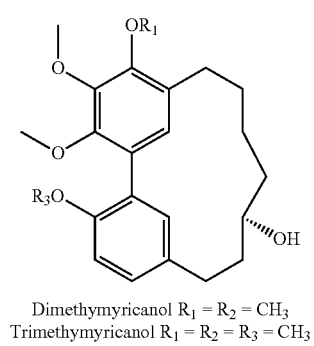

Dimethymyricanol $R_1 = R_2 = CH_3$
Trimethymyricanol $R_1 = R_2 = R_3 = CH_3$

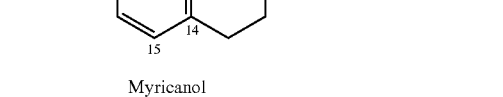

Myricanol 2) 10 mg of myricacene A (trans) was methylated using the same reaction condition and treatment process as the previous reaction. After normal phase HPLC using 25% ethyl acetate and 75% hexane the reaction gave 5 mg of dimethylmyricanone A (trans).

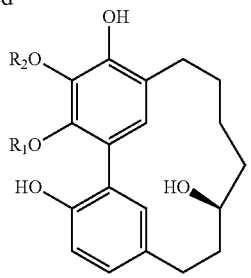

3,4-dihydroxy-myricanol
$R_1 = R_2 = OH$
3-hydroxy-myricanol
$R_1 = OH$  $R_2 = CH_3$
4-hydroxy-myricanol
$R_1 = CH_3$  $R_2 = OH$ Ozonolysis 1) 3 mg of myricacene A (trans) was added to 5 mL of dichloromethane (3 mL) then under an ozone generator during 30 min. The reaction mixture was then treated by dimethyl sulfide for 1 h. The reaction mixture was evaporated and provided 1 mg of dialdehyde A.

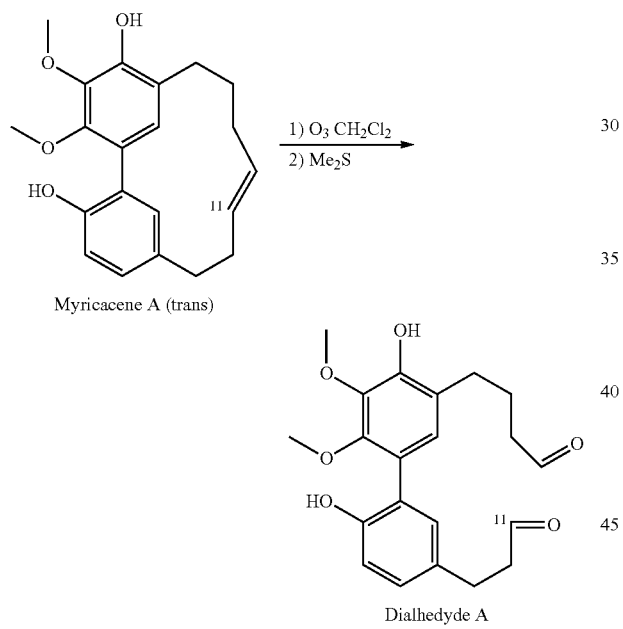

Myricacene A (trans)

Dialhedyde A

2) The same condition as the previous reaction was applied to 3 mg of myricacene B (trans) and gave 0.5 mg dialdehyde A.

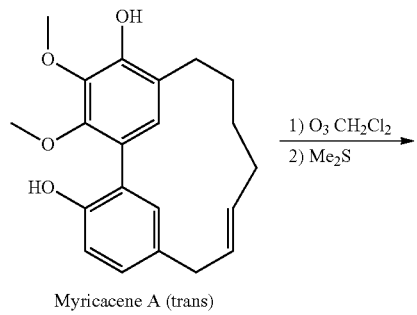

Myricacene A (trans)

dialhedyde B

Esterification

1) Myricanol (100 mg) was treated with a solution of acetone and palmitoyl chloride (127 μL) with potassium carbonate (193 mg) at room temperature for 15 h. The mixture was then concentrated in Vacuo and fractionated on a silica gel column using MPLC (silica cartridge, Isco Combiflash) with a linear gradient of 0-30% ethyl acetate/hexanes.

The major compound eluted was myricanol 11-monopalmitate (21 mg) with an optical rotation of $[\alpha]_D^{21}=44.6$ (c=0.9, Chloroform).

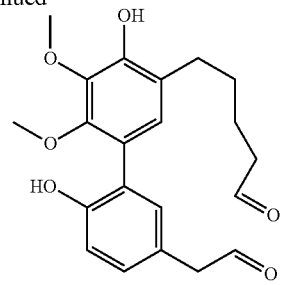

Myricanol

Myricanol 11-palmitate

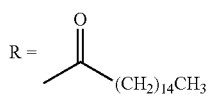

2) Myricanol (100 mg) was added to a solution of pyridine (5 ml) and chloroform (3 mL) with palmitic anhydride (500 mg) at room temperature for 48 h. The mixture was then concentrated in vacuo and fractionated on a silica gel column using MPLC (silica cartridge, Isco Combiflash) with a linear gradient of 0-30% hexane/ethyl Acetate. The major compound eluted was myricanol 17-palmitate Myricanol 5,17-dipalmitate, myricanol 17-palmitate and myricanol 5-palmitate: (+)-S-(60 mg). Myricanol 5-palmitate and myricanol 11,17-dipalmitate were purified using semi-preparative column for normal phase HPLC with a gradient of 0 to 20% Ethyl acetate hexane providing respectively 4 and 6 mg.

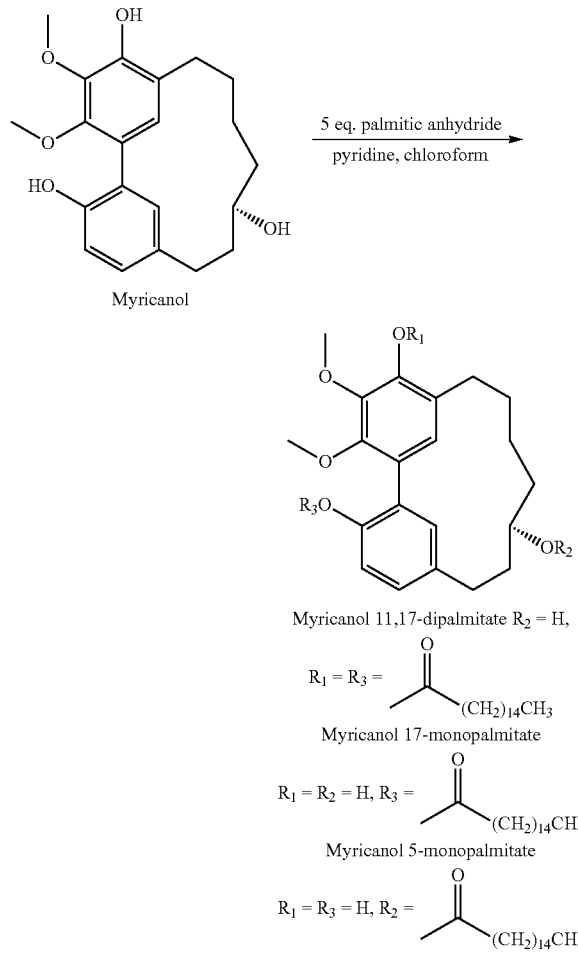

3) Myricacene B (E) (10 mg) was added to a solution of pyridine (5 ml) and chloroform (3 mL) with palmitic anhydride (50 mg) at room temperature for 48 h. The mixture was then concentrated in Vacuo and fractionated on a silica gel column using HPLC a linear gradient of 0-30% Hexane/Ethyl Acetate. The major compound eluted was myricacene B (trans) 5 palmitate,

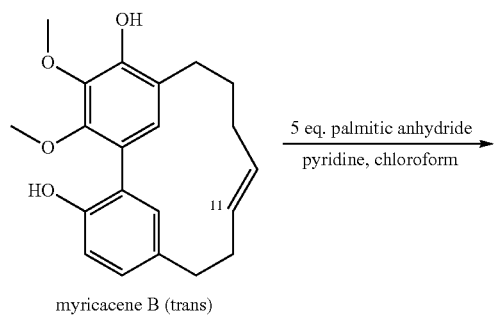

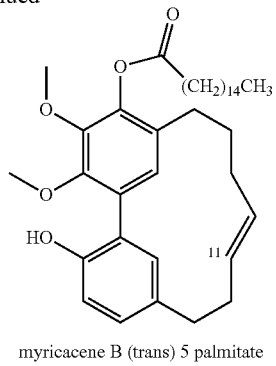

Etherification

The 6-membered-ring derivative (5 mg) and 1 mg of 18-crown-6 were added to a solution of acetonitrile and 1-bromohexadecane (50 µL) with potassium carbonate (193 mg) at room temperature for 24 h. The mixture was diluted with water and diethyl ether, washed with brine. The organic layer was dried over $MgSO_4$, filtered and evaporated. The residue was separated on gradient HPLC (0-30% Ethyl acetate in hexane) to afford 2 mg of dihexadecacyloxy 6-membered ring derivative.

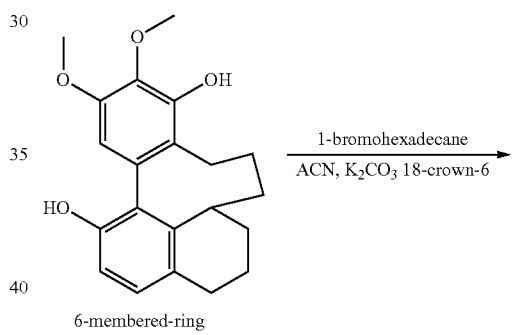

To assess the effects of the aqueous bayberry extract on overexpressed and endogenous tau levels, HeLa cells stably transfected with tau were treated with the myricanol derivatives.

| Compound | Structure | Molecular Weight | Name/ sample names | Results |
|---|---|---|---|---|
| 9 | 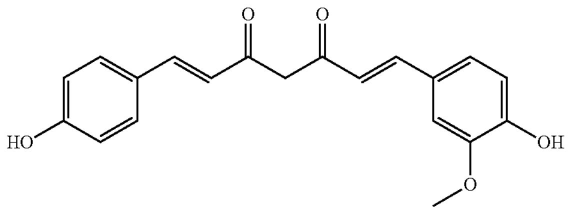 [SMILES: COc1cc(/C=C/C(=O)CC(=O)/C=C/c2ccc(O)cc2)ccc1O] | 338.3539 | Demethoxycurcumin | active |
| 10 | 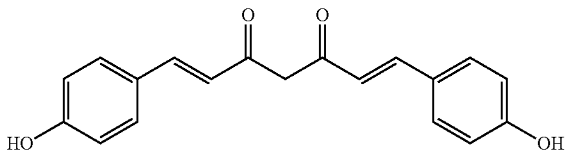 [SMILES: O=C(/C=C/c1ccc(O)cc1)CC(=O)/C=C/c1ccc(O)cc1] | 308.3279 | Bisdemethoxycurcumin | active |
| 11 | 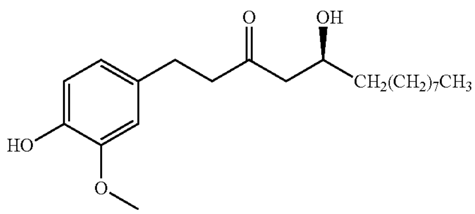 | 350.4923 | [10]-Gingerol | active |
| 18 | 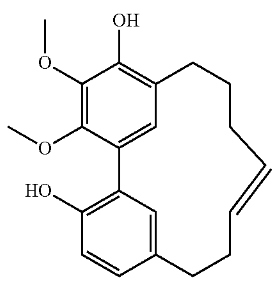 [SMILES: COc1c2cc(c(O)c1OC)CCC/C=C/CCc1ccc(O)c-2c1] | 340.4129 | Myricacene A (trans)/ Myr-R-9-4; Myr-16-13-4 | active |
| 19 | 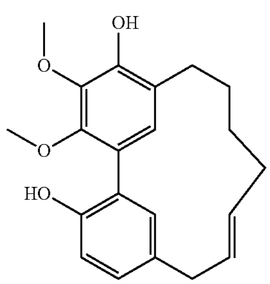 [SMILES: COc1c2cc(c(O)c1OC)CCCC/C=C/Cc1ccc(O)c-2c1] | 340.4129 | Myricacene B (trans)/ Myr-R-9-2-8; Myr-R-16-15 | active |
| 21 | 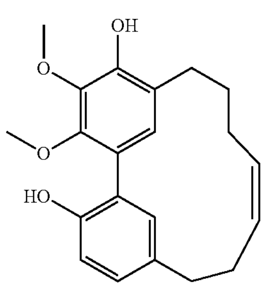 [SMILES: COc1c2cc(c(O)c1OC)CCC/C=C\CCc1ccc(O)c-2c1] | 340.4129 | Myricacene A (cis)/ Myr-R-9-2-4; Myr-R-16-13-2 | moderately active |

-continued

| Compound | Structure | Molecular Weight | Name/ sample names | Results |
|---|---|---|---|---|
| 22 | 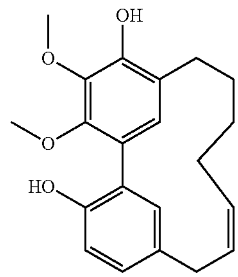 [SMILES: COc1c2cc(c(O)c1OC)CCCC/C=C\Cc1ccc(O)c-2c1] | 340.4129 | Myricacene B (cis)/ Myr-R-9-2-6 | active |
| 23 | 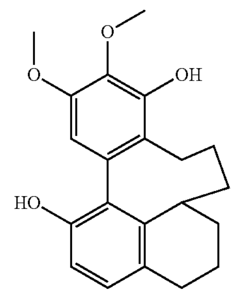 [SMILES: COc1cc2c(c(O)c1OC)CCCC1CCCc3ccc(O)c-2c31] | 340.4129 | Myr-R-16-6 | very active |
| 24 | 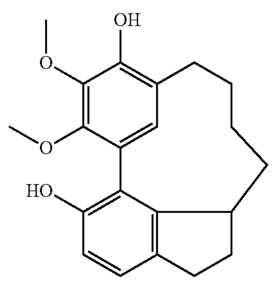 [SMILES: COc1c2cc(c(O)c1OC)CCCCC1CCc3ccc(O)c-2c31] | 340.4129 | Myr-R-16-4-2 | active |

The results show that myricanol derivatives myricacene B (cis) (Compound 22) and the 6-membered ring (Compound 23) potently reduce levels of tau proteins, and thus, can be used to treat tauopathies such as Alzheimer's disease.

Time-dependent bioassay revealed that the 6-membered-ring derivative (Compound 23) potently reduces protein tau levels upon treatment of HeLa cells for 24 hours. Dose-dependent bioassay revealed that myricacene B (cis) (Compound 22) is a potent tau-reducing compound at a concentration of 20 μg/mL. The active synthesized compounds exhibit low toxicity and do not alter the amount of glyceraldehyde 3-phosphate dehydrogenase (GADPH) levels (they also showed an $IC_{50}$ against A549>10 μg/mL).

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

All patents, patent applications, provisional applications, and publications referred to or cited herein are incorporated by reference in their entirety, including all figures and Tables, to the extent they are not inconsistent with the explicit teachings of this specification.

The invention claimed is:

1. A method of reducing intracellular tau levels, wherein said method comprises administering, to cells comprising protein tau, an effective amount of a compound of formula B:

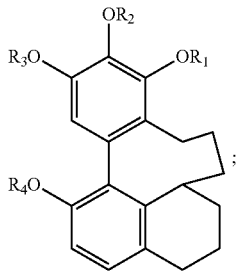

(B)

wherein each of $R_1$-$R_4$ is, independently, —H or any group that forms an ester or ether bond or a salt thereof; and
whereby intracellular tau level is reduced.

2. The method according to claim 1, wherein the compound of formula B is Compound 23:

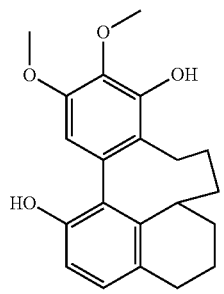 [SMILES: COc1cc2c(c(O)c1OC)CCCC1CCCc3ccc(O)c-2c31]

or a salt thereof.

3. The method according to claim 1, wherein the compound of formula B has the following structure:

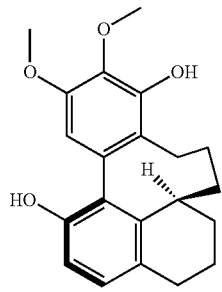

4. The method according to claim 1, wherein the cells are in a subject in need of treatment for a neurodegenerative disease.

5. The method of claim 4, wherein the neurodegenerative disease is a tauopathy.

6. The method of claim 5, wherein the subject is a human.

7. The method of claim 6, wherein the neurodegenerative disease is selected from Alzheimer's disease, Parkinson's disease, frontotemporal dementia, frontotemporal dementia with Parkinsonism, frontotemporal lobe dementia, pallido-pontonigral degeneration, progressive supranuclear palsy, multiple system tauopathy, multiple system tauopathy with presenile dementia, Wilhelmsen-Lynch disease, Pick's disease, and Pick's disease-like dementia.

8. The method of claim 7, wherein the neurodegenerative disease is Alzheimer's disease.

* * * * *

SEQUENCE LISTING

<160> NUMBER OF SEQ ID NOS: 6

<210> SEQ ID NO 1
<211> LENGTH: 352
<212> TYPE: PRT
<213> ORGANISM: Homo sapiens

<400> SEQUENCE: 1

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
    130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Val Tyr Lys Pro Val
    210                 215                 220

Asp Leu Ser Lys Val Thr Ser Lys Cys Gly Ser Leu Gly Asn Ile His
225                 230                 235                 240

His Lys Pro Gly Gly Gly Gln Val Glu Val Lys Ser Glu Lys Leu Asp
                245                 250                 255

Phe Lys Asp Arg Val Gln Ser Lys Ile Gly Ser Leu Asp Asn Ile Thr
            260                 265                 270

His Val Pro Gly Gly Gly Asn Lys Lys Ile Glu Thr His Lys Leu Thr
        275                 280                 285

Phe Arg Glu Asn Ala Lys Ala Lys Thr Asp His Gly Ala Glu Ile Val
    290                 295                 300

Tyr Lys Ser Pro Val Val Ser Gly Asp Thr Ser Pro Arg His Leu Ser
305                 310                 315                 320

Asn Val Ser Ser Thr Gly Ser Ile Asp Met Val Asp Ser Pro Gln Leu
                325                 330                 335

Ala Thr Leu Ala Asp Glu Val Ser Ala Ser Leu Ala Lys Gln Gly Leu
            340                 345                 350

<210> SEQ ID NO 2
<211> LENGTH: 441
<212> TYPE: PRT
<213> ORGANISM: Homo sapiens

<400> SEQUENCE: 2

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30
```

```
            Gln Asp Gln Glu Gly Asp Thr Asp Ala Gly Leu Lys Glu Ser Pro Leu
                     35                  40                  45

Gln Thr Pro Thr Glu Asp Gly Ser Glu Glu Pro Gly Ser Glu Thr Ser
             50                  55                  60

Asp Ala Lys Ser Thr Pro Thr Ala Glu Asp Val Thr Ala Pro Leu Val
             65                  70                  75                  80

Asp Glu Gly Ala Pro Gly Lys Gln Ala Ala Gln Pro His Thr Glu
                             85                  90                  95

Ile Pro Glu Gly Thr Thr Ala Glu Glu Ala Gly Ile Gly Asp Thr Pro
                            100                 105                 110

Ser Leu Glu Asp Glu Ala Ala Gly His Val Thr Gln Ala Arg Met Val
                        115                 120                 125

Ser Lys Ser Lys Asp Gly Thr Gly Ser Asp Asp Lys Lys Ala Lys Gly
                    130                 135                 140

Ala Asp Gly Lys Thr Lys Ile Ala Thr Pro Arg Gly Ala Ala Pro Pro
            145                 150                 155                 160

Gly Gln Lys Gly Gln Ala Asn Ala Thr Arg Ile Pro Ala Lys Thr Pro
                            165                 170                 175

Pro Ala Pro Lys Thr Pro Ser Ser Gly Glu Pro Lys Ser Gly
                        180                 185                 190

Asp Arg Ser Gly Tyr Ser Ser Pro Gly Ser Pro Gly Thr Pro Gly Ser
                        195                 200                 205

Arg Ser Arg Thr Pro Ser Leu Pro Thr Pro Thr Arg Glu Pro Lys
                    210                 215                 220

Lys Val Ala Val Val Arg Thr Pro Pro Lys Ser Pro Ser Ser Ala Lys
            225                 230                 235                 240

Ser Arg Leu Gln Thr Ala Pro Val Pro Met Pro Asp Leu Lys Asn Val
                            245                 250                 255

Lys Ser Lys Ile Gly Ser Thr Glu Asn Leu Lys His Gln Pro Gly Gly
                        260                 265                 270

Gly Lys Val Gln Ile Ile Asn Lys Lys Leu Asp Leu Ser Asn Val Gln
                    275                 280                 285

Ser Lys Cys Gly Ser Lys Asp Asn Ile Lys His Val Pro Gly Gly Gly
                290                 295                 300

Ser Val Gln Ile Val Tyr Lys Pro Val Asp Leu Ser Lys Val Thr Ser
            305                 310                 315                 320

Lys Cys Gly Ser Leu Gly Asn Ile His His Lys Pro Gly Gly Gly Gln
                            325                 330                 335

Val Glu Val Lys Ser Glu Lys Leu Asp Phe Lys Asp Arg Val Gln Ser
                        340                 345                 350

Lys Ile Gly Ser Leu Asp Asn Ile Thr His Val Pro Gly Gly Gly Asn
                    355                 360                 365

Lys Lys Ile Glu Thr His Lys Leu Thr Phe Arg Glu Asn Ala Lys Ala
                370                 375                 380

Lys Thr Asp His Gly Ala Glu Ile Val Tyr Lys Ser Pro Val Val Ser
            385                 390                 395                 400

Gly Asp Thr Ser Pro Arg His Leu Ser Asn Val Ser Ser Thr Gly Ser
                            405                 410                 415

Ile Asp Met Val Asp Ser Pro Gln Leu Ala Thr Leu Ala Asp Glu Val
                        420                 425                 430

Ser Ala Ser Leu Ala Lys Gln Gly Leu
                    435                 440
```

<210> SEQ ID NO 3
<211> LENGTH: 383
<212> TYPE: PRT
<213> ORGANISM: Homo sapiens

<400> SEQUENCE: 3

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
    130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Ile Asn Lys Lys Leu
    210                 215                 220

Asp Leu Ser Asn Val Gln Ser Lys Cys Gly Ser Lys Asp Asn Ile Lys
225                 230                 235                 240

His Val Pro Gly Gly Gly Ser Val Gln Ile Val Tyr Lys Pro Val Asp
                245                 250                 255

Leu Ser Lys Val Thr Ser Lys Cys Gly Ser Leu Gly Asn Ile His His
            260                 265                 270

Lys Pro Gly Gly Gly Gln Val Glu Val Lys Ser Glu Lys Leu Asp Phe
        275                 280                 285

Lys Asp Arg Val Gln Ser Lys Ile Gly Ser Leu Asp Asn Ile Thr His
    290                 295                 300

Val Pro Gly Gly Gly Asn Lys Lys Ile Glu Thr His Lys Leu Thr Phe
305                 310                 315                 320

Arg Glu Asn Ala Lys Ala Lys Thr Asp His Gly Ala Glu Ile Val Tyr
                325                 330                 335

Lys Ser Pro Val Val Ser Gly Asp Thr Ser Pro Arg His Leu Ser Asn
            340                 345                 350

Val Ser Ser Thr Gly Ser Ile Asp Met Val Asp Ser Pro Gln Leu Ala
        355                 360                 365

Thr Leu Ala Asp Glu Val Ser Ala Ser Leu Ala Lys Gln Gly Leu
    370                 375                 380

<210> SEQ ID NO 4
<211> LENGTH: 758
<212> TYPE: PRT
<213> ORGANISM: Homo sapiens

<400> SEQUENCE: 4

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
        195                 200                 205

Lys Glu Arg Pro Gly Ser Lys Glu Glu Val Asp Glu Asp Arg Asp Val
    210                 215                 220

Asp Glu Ser Ser Pro Gln Asp Ser Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
        275                 280                 285

Val Gly Arg Ala Lys Gly Gln Asp Ala Pro Leu Glu Phe Thr Phe His
    290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
            340                 345                 350

Glu Pro Ser Glu Lys Gln Pro Ala Ala Ala Pro Arg Gly Lys Pro Val
        355                 360                 365

Ser Arg Val Pro Gln Leu Lys Ala Arg Met Val Ser Lys Ser Lys Asp
```

```
                370                 375                 380
Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys His Pro Thr
                405                 410                 415

Pro Gly Ser Ser Asp Pro Leu Ile Gln Pro Ser Ser Pro Ala Val Cys
            420                 425                 430

Pro Glu Pro Pro Ser Ser Pro Lys Tyr Val Ser Ser Val Thr Ser Arg
        435                 440                 445

Thr Gly Ser Ser Gly Ala Lys Glu Met Lys Leu Lys Gly Ala Asp Gly
    450                 455                 460

Lys Thr Lys Ile Ala Thr Pro Arg Gly Ala Ala Pro Pro Gly Gln Lys
465                 470                 475                 480

Gly Gln Ala Asn Ala Thr Arg Ile Pro Ala Lys Thr Pro Pro Ala Pro
                485                 490                 495

Lys Thr Pro Pro Ser Ser Gly Glu Pro Pro Lys Ser Gly Asp Arg Ser
            500                 505                 510

Gly Tyr Ser Ser Pro Gly Ser Pro Gly Thr Pro Gly Ser Arg Ser Arg
        515                 520                 525

Thr Pro Ser Leu Pro Thr Pro Pro Thr Arg Glu Pro Lys Lys Val Ala
    530                 535                 540

Val Val Arg Thr Pro Pro Lys Ser Pro Ser Ser Ala Lys Ser Arg Leu
545                 550                 555                 560

Gln Thr Ala Pro Val Pro Met Pro Asp Leu Lys Asn Val Lys Ser Lys
                565                 570                 575

Ile Gly Ser Thr Glu Asn Leu Lys His Gln Pro Gly Gly Gly Lys Val
            580                 585                 590

Gln Ile Ile Asn Lys Lys Leu Asp Leu Ser Asn Val Gln Ser Lys Cys
        595                 600                 605

Gly Ser Lys Asp Asn Ile Lys His Val Pro Gly Gly Gly Ser Val Gln
    610                 615                 620

Ile Val Tyr Lys Pro Val Asp Leu Ser Lys Val Thr Ser Lys Cys Gly
625                 630                 635                 640

Ser Leu Gly Asn Ile His His Lys Pro Gly Gly Gly Gln Val Glu Val
                645                 650                 655

Lys Ser Glu Lys Leu Asp Phe Lys Asp Arg Val Gln Ser Lys Ile Gly
            660                 665                 670

Ser Leu Asp Asn Ile Thr His Val Pro Gly Gly Gly Asn Lys Lys Ile
        675                 680                 685

Glu Thr His Lys Leu Thr Phe Arg Glu Asn Ala Lys Ala Lys Thr Asp
    690                 695                 700

His Gly Ala Glu Ile Val Tyr Lys Ser Pro Val Val Ser Gly Asp Thr
705                 710                 715                 720

Ser Pro Arg His Leu Ser Asn Val Ser Ser Thr Gly Ser Ile Asp Met
                725                 730                 735

Val Asp Ser Pro Gln Leu Ala Thr Leu Ala Asp Glu Val Ser Ala Ser
            740                 745                 750

Leu Ala Lys Gln Gly Leu
        755

<210> SEQ ID NO 5
<211> LENGTH: 776
<212> TYPE: PRT
<213> ORGANISM: Homo sapiens
```

<400> SEQUENCE: 5

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
        195                 200                 205

Lys Glu Arg Pro Gly Ser Lys Glu Glu Val Asp Glu Asp Arg Asp Val
    210                 215                 220

Asp Glu Ser Ser Pro Gln Asp Ser Pro Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
        275                 280                 285

Val Gly Arg Ala Lys Gly Gln Asp Ala Pro Leu Glu Phe Thr Phe His
    290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
            340                 345                 350

Glu Pro Ser Glu Lys Gln Pro Ala Ala Pro Arg Gly Lys Pro Val
        355                 360                 365

Ser Arg Val Pro Gln Leu Lys Ala Arg Met Val Ser Lys Ser Lys Asp
    370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys His Pro Thr
```

405                 410                 415
Pro Gly Ser Ser Asp Pro Leu Ile Gln Pro Ser Ser Pro Ala Val Cys
            420                 425                 430
Pro Glu Pro Pro Ser Ser Pro Lys Tyr Val Ser Ser Val Thr Ser Arg
            435                 440                 445
Thr Gly Ser Ser Gly Ala Lys Glu Met Lys Leu Lys Gly Ala Asp Gly
        450                 455                 460
Lys Thr Lys Ile Ala Thr Pro Arg Gly Ala Ala Pro Pro Gly Gln Lys
465                 470                 475                 480
Gly Gln Ala Asn Ala Thr Arg Ile Pro Ala Lys Thr Pro Pro Ala Pro
                485                 490                 495
Lys Thr Pro Pro Ser Ser Ala Thr Lys Gln Val Gln Arg Arg Pro Pro
            500                 505                 510
Pro Ala Gly Pro Arg Ser Glu Arg Gly Glu Pro Pro Lys Ser Gly Asp
            515                 520                 525
Arg Ser Gly Tyr Ser Ser Pro Gly Ser Pro Gly Thr Pro Gly Ser Arg
            530                 535                 540
Ser Arg Thr Pro Ser Leu Pro Thr Pro Pro Thr Arg Glu Pro Lys Lys
545                 550                 555                 560
Val Ala Val Val Arg Thr Pro Pro Lys Ser Pro Ser Ser Ala Lys Ser
                565                 570                 575
Arg Leu Gln Thr Ala Pro Val Pro Met Pro Asp Leu Lys Asn Val Lys
                580                 585                 590
Ser Lys Ile Gly Ser Thr Glu Asn Leu Lys His Gln Pro Gly Gly Gly
            595                 600                 605
Lys Val Gln Ile Ile Asn Lys Lys Leu Asp Leu Ser Asn Val Gln Ser
610                 615                 620
Lys Cys Gly Ser Lys Asp Asn Ile Lys His Val Pro Gly Gly Gly Ser
625                 630                 635                 640
Val Gln Ile Val Tyr Lys Pro Val Asp Leu Ser Lys Val Thr Ser Lys
                645                 650                 655
Cys Gly Ser Leu Gly Asn Ile His His Lys Pro Gly Gly Gly Gln Val
                660                 665                 670
Glu Val Lys Ser Glu Lys Leu Asp Phe Lys Asp Arg Val Gln Ser Lys
            675                 680                 685
Ile Gly Ser Leu Asp Asn Ile Thr His Val Pro Gly Gly Gly Asn Lys
            690                 695                 700
Lys Ile Glu Thr His Lys Leu Thr Phe Arg Glu Asn Ala Lys Ala Lys
705                 710                 715                 720
Thr Asp His Gly Ala Glu Ile Val Tyr Lys Ser Pro Val Val Ser Gly
                725                 730                 735
Asp Thr Ser Pro Arg His Leu Ser Asn Val Ser Ser Thr Gly Ser Ile
            740                 745                 750
Asp Met Val Asp Ser Pro Gln Leu Ala Thr Leu Ala Asp Glu Val Ser
            755                 760                 765
Ala Ser Leu Ala Lys Gln Gly Leu
            770                 775

<210> SEQ ID NO 6
<211> LENGTH: 412
<212> TYPE: PRT
<213> ORGANISM: Homo sapiens

<400> SEQUENCE: 6

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
50                  55                  60

Asp Ala Lys Ser Thr Pro Thr Ala Glu Ala Glu Ala Gly Ile Gly
65                  70                  75                  80

Asp Thr Pro Ser Leu Glu Asp Glu Ala Ala Gly His Val Thr Gln Ala
                85                  90                  95

Arg Met Val Ser Lys Ser Lys Asp Gly Thr Gly Ser Asp Asp Lys Lys
            100                 105                 110

Ala Lys Gly Ala Asp Gly Lys Thr Lys Ile Ala Thr Pro Arg Gly Ala
        115                 120                 125

Ala Pro Pro Gly Gln Lys Gly Gln Ala Asn Ala Thr Arg Ile Pro Ala
    130                 135                 140

Lys Thr Pro Pro Ala Pro Lys Thr Pro Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Pro Thr Arg
            180                 185                 190

Glu Pro Lys Lys Val Ala Val Val Arg Thr Pro Pro Lys Ser Pro Ser
        195                 200                 205

Ser Ala Lys Ser Arg Leu Gln Thr Ala Pro Val Pro Met Pro Asp Leu
    210                 215                 220

Lys Asn Val Lys Ser Lys Ile Gly Ser Thr Glu Asn Leu Lys His Gln
225                 230                 235                 240

Pro Gly Gly Gly Lys Val Gln Ile Ile Asn Lys Lys Leu Asp Leu Ser
                245                 250                 255

Asn Val Gln Ser Lys Cys Gly Ser Lys Asp Asn Ile Lys His Val Pro
            260                 265                 270

Gly Gly Gly Ser Val Gln Ile Val Tyr Lys Pro Val Asp Leu Ser Lys
        275                 280                 285

Val Thr Ser Lys Cys Gly Ser Leu Gly Asn Ile His His Lys Pro Gly
    290                 295                 300

Gly Gly Gln Val Glu Val Lys Ser Glu Lys Leu Asp Phe Lys Asp Arg
305                 310                 315                 320

Val Gln Ser Lys Ile Gly Ser Leu Asp Asn Ile Thr His Val Pro Gly
                325                 330                 335

Gly Gly Asn Lys Lys Ile Glu Thr His Lys Leu Thr Phe Arg Glu Asn
            340                 345                 350

Ala Lys Ala Lys Thr Asp His Gly Ala Glu Ile Val Tyr Lys Ser Pro
        355                 360                 365

Val Val Ser Gly Asp Thr Ser Pro Arg His Leu Ser Asn Val Ser Ser
    370                 375                 380

Thr Gly Ser Ile Asp Met Val Asp Ser Pro Gln Leu Ala Thr Leu Ala
385                 390                 395                 400

Asp Glu Val Ser Ala Ser Leu Ala Lys Gln Gly Leu
                405                 410
```